United States Patent
Kita et al.

(10) Patent No.: US 9,078,953 B2
(45) Date of Patent: Jul. 14, 2015

(54) CROSSLINKED HYDROGELS

(75) Inventors: Kristin B. Kita, Conshohocken, PA (US); Nigel G. Smith, Norwian (GB); Anthony M. Lowman, Wallingford, PA (US); Garland W. Fussell, Thorndale, PA (US); Michael F. Keane, Downingtown, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 497 days.

(21) Appl. No.: 12/747,411

(22) PCT Filed: Dec. 16, 2008

(86) PCT No.: PCT/US2008/086997
§ 371 (c)(1),
(2), (4) Date: Jun. 10, 2010

(87) PCT Pub. No.: WO2009/079507
PCT Pub. Date: Jun. 25, 2009

(65) Prior Publication Data
US 2010/0272672 A1    Oct. 28, 2010

Related U.S. Application Data

(60) Provisional application No. 61/014,347, filed on Dec. 17, 2007.

(51) Int. Cl.
*A61K 31/79* (2006.01)
*A61K 31/785* (2006.01)
*A61P 43/00* (2006.01)
*A61L 27/16* (2006.01)

(52) U.S. Cl.
CPC ...................................... *A61L 27/16* (2013.01)

(58) Field of Classification Search
None
See application file for complete search history.

(56) References Cited

U.S. PATENT DOCUMENTS

| | | | | |
|---|---|---|---|---|
| 4,241,682 A | | 12/1980 | Konstandt | 114/67 R |
| 5,171,775 A | * | 12/1992 | Graiver et al. | 524/503 |
| 5,306,504 A | * | 4/1994 | Lorenz | 424/449 |
| 6,818,018 B1 | * | 11/2004 | Sawhney | 623/11.11 |
| 2004/0170612 A1 | * | 9/2004 | Griffith et al. | 424/93.7 |
| 2007/0150060 A1 | | 6/2007 | Trieu | 623/17.12 |

FOREIGN PATENT DOCUMENTS

| | | | | |
|---|---|---|---|---|
| JP | 4334539 | * | 11/1992 | A61L 27/00 |
| WO | WO 02/065963 | | 8/2002 | A61F 13/00 |
| WO | WO02/065963 | * | 8/2002 | A61F 13/00 |
| WO | WO 2008/024771 | | 2/2008 | A61L 27/50 |

OTHER PUBLICATIONS

Shim et al. "Preparation of Hydrogels Composed of Poly(vinyl alcohol) and Polyethleneimine and Their Electrical Properties", Journal of Applied Polymer Science, 107, 2007, pp. 2136-2141.*
Rao et al. "Dehydration of Tetrahydrofuran by Pervaporation Using Crosslinked PVA/PEI Blend Membranes", Journal of Applied Polymer Science, 102, 2006, pp. 1152-1161.*
International Search Report and Written Opinion, mailed on Mar. 3, 2010, for PCT international Application No. PCT/US2008/086997, filed on Dec. 16, 2008.

* cited by examiner

*Primary Examiner* — Kortney L Klinkel
*Assistant Examiner* — Melissa Javier
(74) *Attorney, Agent, or Firm* — Nutter McClennen & Fish LLP

(57) ABSTRACT

The present invention preferably provides for a method of forming and the resulting solid polymer gel composition comprising polyethylene imine and at least one hydrogen bonding polymer. The composition has a greater viscosity than either of the polyethylene imine or the hydrogen bonding polymer alone and is injectable immediately after mixing of the polyethylene imine and the at least one hydrogen bonding polymer. A method of tissue repair may include mixing about 9.25% (w/w) to about 13.65% (w/w) polyethylene imine and about 18.02% (w/w) to about 26.62% (w/w) polyvinyl alcohol to form an injectable composition; injecting the injectable composition into a cavity within a human body; and allowing the composition to solidify in situ. A kit may include a multi-barrel syringe at least one barrel is loaded with polyethylene imine and at least another barrel is loaded with at least one hydrogen bonding polymer.

16 Claims, 6 Drawing Sheets

CROSSLINKED HYDROGELS

CROSS-REFERENCE TO RELATED APPLICATIONS

This application claims the benefit of U.S. Provisional Application No. 61/014,347, filed on Dec. 17, 2007, entitled "CROSSLINKED HYDROGELS," the contents of which is incorporated in its entirety by reference herein.

BACKGROUND OF THE INVENTION

The human intervertebral disc comprises an outer or peripheral tendinous structure which encircles an inner gelatinous nucleus pulposus material. Loss of structural integrity in the disc results in a dehydration and degeneration of these tissues, which leads to a loss in function of the disc.

Chronic back pain as a result of the aforementioned degeneration is a common symptom in patients. Current treatments range from bed rest to highly invasive surgical procedures, including spinal fusion and total disc replacement. Further, pain may be mitigated and healthy physiologic function may be restored to the spine through the replacement or supplementation of nucleus pulposus tissue. The crosslinked hydrogels described herein may have application in such replacement or supplementation of nucleus pulposus tissue and other bioapplications.

Although polymeric compositions comprising a single polymer can be formulated to form solids, the resultant composition would have a total polymer concentration which is much higher than the embodiments of the present invention and also would not be injectable.

BRIEF SUMMARY OF THE INVENTION

The present invention relates to a method of forming, and the resulting solidifying polymer gel and intermediaries thereof, for use as a soft-tissue replacement, supplement or repair, an implant rigid construct, scaffold and/or bioadhesive or in vertebroplasty One embodiment of the present invention may comprise a polymer gel composition comprising polyethylene imine and at least one hydrogen bonding polymer, the composition having a greater viscosity than either of the polyethylene imine or the hydrogen bonding polymer alone. Both the polyethylene imine and the at least one hydrogen bonding polymer may have an appropriate viscosity and properties, prior to mixing, to be injectable at room temperature or under operating room conditions. The composition may also be injectable immediately after mixing of the polyethylene imine and the at least one hydrogen bonding polymer, but thereafter solidify into a moldable form. The composition may be injectable after mixing but may thereafter solidify in situ in the patient. The hydrogen bonding polymer may include polyvinyl alcohol, polyethylene glycol, polyethylene oxide, polyvinyl pyrrolidone, polyacrylamide, polyhydroxyethylmethacrylate, polyacrylic acid, polymethacrylic acid or combinations thereof.

A further embodiment of the present invention may comprise a polymer gel comprising about 9.25% (w/w) to about 13.65% (w/w) polyethylene imine and at least one hydrogen bonding polymer, the composition having a greater viscosity than either the polyethylene imine or the hydrogen bonding polymer alone. Both the polyethylene imine and the at least one hydrogen bonding polymer may have suitable viscosity and other properties, prior to mixing, to be injectable immediately after mixing but thereafter solidify into a moldable form. The composition may be injectable after mixing but may thereafter solidify in situ in the patient.

A still further embodiment of the present invention may comprise a polymer gel comprising polyethylene imine and about 18.02% (w/w) to about 26.62% (w/w) of a hydrogen bonding polymer, the composition having a greater viscosity than either of the polyethylene imine and the at lest one hydrogen bonding polymer alone. Both the polyethylene imine and the at least one hydrogen bonding polymer may have suitable viscosity and other properties, prior to mixing, to be injectable immediately after mixing but thereafter solidify into a moldable form and/or solidify in situ in the patient.

Another embodiment of the present invention may comprise a solid polymer gel comprising polyethylene imine and about 18.02% (w/w) to about 26.62% (w/w) polyvinyl alcohol, the composition having a greater viscosity than either of the polyethylene imine and the polyvinyl alcohol alone. Both the polyethylene imine and the at least one hydrogen bonding polymer may have suitable viscosity and other properties, prior to mixing, to be injectable immediately after mixing but thereafter solidify into a moldable form and/or solidify in situ in the patient.

A further embodiment of the present invention may include a solid polymer gel composition comprising about 9.25% (w/w) to about 13.65% (w/w) polyethylene imine and about 18.02% (w/w) to about 26.62% (w/w) polyvinyl alcohol, the composition having a greater viscosity than either of the polyethylene imine or the polyvinyl alcohol alone. The composition may be injectable immediately after mixing of the polyethylene imine and the polyvinyl alcohol. The composition may be injectable after mixing but may thereafter solidify into a moldable form and/or solidify in situ in the patient. The composition preferably remains injectable for sufficient time to be implanted during a medical procedure but thereafter solidify relatively quickly in situ after being implanted.

In another embodiment of the invention there is provided a method of forming a solid polymer gel composition comprising: providing polyethylene imine having appropriate viscosity and properties to be injectable at room temperature or under operating room conditions; providing at least one hydrogen bonding polymer having appropriate viscosity and properties to be injectable at room temperature or under operating room conditions; mixing the polyethylene imine and the at least one hydrogen bonding polymer wherein the viscosity of the mixed components is greater than the viscosity of either of the polyethylene imine or the at least one hydrogen bonding polymer prior to mixing and wherein the polymer gel composition solidifies at a lower polymer content than the at least one hydrogen bonding composition would solidify if used without polyethylene imine.

Another embodiment of the present invention may include a method of tissue repair comprising: mixing about 9.25% (w/w) to about 13.65% (w/w) polyethylene imine and about 18.02% (w/w) to about 26.62% (w/w) polyvinyl alcohol to form an injectable composition; injecting the injectable composition into a cavity within a mammalian body; and allowing the composition to solidify in situ.

In yet another embodiment of the present invention there is provided a kit comprising: a multi-barrel syringe, wherein one of the barrel may be loaded with polyethylene imine at a sufficient concentration to be injectable at room temperature or under operating room conditions and wherein at least one of the barrels to be loaded with a hydrogen bonding polymer at a sufficient concentration to be injectable at room temperature or under operating room conditions.

The above described embodiments are only illustrative and exemplary in nature and are not intended to limit or define the scope of the invention.

BRIEF DESCRIPTION OF THE DRAWINGS

The foregoing summary, as well as the following detailed description of the preferred embodiments of the application, will be better understood when read in conjunction with the appended drawings. The drawings, examples and embodiments described within this specification are to be understood as illustrative and exemplary of structures, features and aspects of the present invention and not as limiting the scope of the invention. It should be understood that the application is not limited to the precise arrangements and instrumentalities shown. In the drawings.

DETAILED DESCRIPTION OF THE INVENTION

Figure 1:
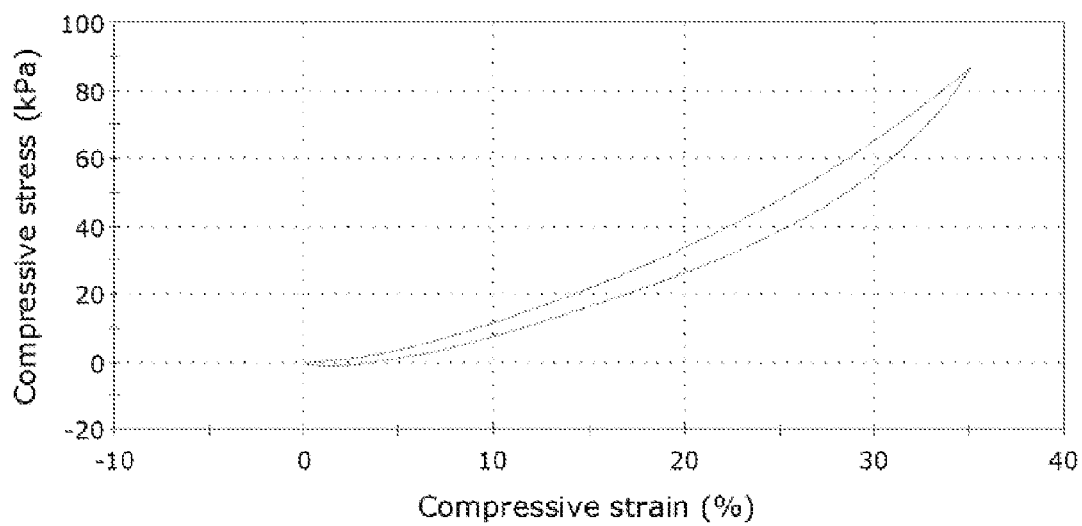
FIG. 1 is a graphical representation of the compression testing data of sample compositions which have been molded into cylinders.

The methods, examples and embodiments described within this specification are to be understood as illustrative and exemplary of structures, features and aspects of the present invention and not as limiting the scope of the invention.

One exemplary embodiment of the present invention is directed to a method of forming and the resultant solid polymer gel composition which has a greater viscosity than any of the individual components of the composition. The polymer gel composition may be injectable immediately after mixing of the components, but may thereafter solidify into a moldable form and/or solidify in situ in a patient.

Due to their high water-content and ability to mimic native physiologic tissues, hydrogels are valuable for the development of synthetic materials for nucleus pulposus replacement, as well as for tissue replacement and augmentation at a variety of other sites within the body. The development of physically-crosslinked structures is valuable, so as to avoid the inclusion of toxic crosslinking agents used in the formation of many chemical networks. The composition of the present invention may contain dense physically crosslinked networks through enhanced hydrogen-bonding.

The combination of multiple components that produce an enhanced hydrogen-bonded effect such as with the composition of the present invention has not been previously disclosed, and further, the use of two injectable components that form a solid hydrogel structure with desirable mechanical and elastic properties through spontaneous enhanced physical crosslinking has also not been previously disclosed.

An embodiment of the present invention may comprise an injectable multi-component system, in which one component includes PEI or a similar cationic polymer. The second component may comprise an aqueous solution of a hydrophilic, ionic or hydrogen bonding polymer such as, but not limited to, PVA, polyethylene glycol(PEG), polyethylene oxide (PEO) (including hyperbranched varieties), polyvinyl pyrrolidone(PVP), polyacrylamide(PAAm), polyhydroxyethylmethacrylate(PHEMA), polyacrylic acid(PAA) and polymethacrylic acid(PMA). Combinations of hydrophilic components (mixtures or copolymers) such as, for example, 99:1 polyvinyl alcohol:polyvinyl pyrrolidone are also anticipated.

A further embodiment of the present invention is an injectable multi-component composition comprising about 9.25% (w/w) to about 13.65% (w/w) PEI, preferably about 10.2% (w/w) to about 12.4% (w/w) PEI, more preferably about 11.4% (w/w) to about 11.8% (w/w) PEI and also comprising about 18.02% (w/w) to about 26.62% (w/w) PVA, preferably about 19.7% (w/w) to about 23.3% (w/w) PVA and more preferably about 22.1% (w/w) to about 22.6% (w/w) PVA.

Primary and secondary amine groups such as those on polyethylene imine (PEI) are known to form strong hydrogen bonds and are highly associated in the liquid state. Polyvinyl alcohol (PVA) similarly forms hydrogen bonds. Both polymers are miscible in water and a solution of a single phase is formed when PEI is mixed with aqueous PVA solution.

An embodiment of the present invention is a polymer gel which may consist of two lower viscosity components that combine to result in a composition with a viscosity that is greater than either two components alone. This synergistic effect is evidenced by significant increases in compressive modulus in the solidified gel and physically-crosslinked network that stabilizes the gel formed from the two components. An aspect of the subject application is the injectability of the two components, as well as the injectability of the final composition immediately following the mixing of the individual components. This allows the composition to be injected into a mammalian body before it solidifies into the resulting gel formulation. The polymer composition of the present invention may solidify into the resulting gel formulation in about 5 minutes to about 32 hours, preferably between 20 minutes and 16 hours and more preferably between 45 minutes and 8 hours. It will be readily understood by one of ordinary skill in the art that the polymer composition preferably remains injectable during a surgical procedure.

The combination of a lower viscosity polymer such as, for example, PEI, to a polymer capable of hydrogen bonding, such as, for example, PVA, crosslinks and stabilizes the gel via an enhanced hydrogen bonding effect, in order to impart a setting behavior. This was a surprising result because there was no prior indication that the combination of the two viscous components would result in formation of an elastic network. Adding PEI permits the increase in the overall polymer content without sacrificing the injectable nature of the composition. The multi-component system may be mixed together prior to injection, or during the injection process through, for example, the use of a conventional static mixer.

The materials, including the polymer components, may be provided as a kit in separate containers so that the polymers can be readily mixed just before or during the medical procedure. In one embodiment the polyethylene imine may be provided in an at least one first container loaded with polyethylene imine at a sufficient concentration to be injectable at room temperature or under operating room conditions and the at least one hydrogen bonding polymer may be provided in at least one second container loaded with at least one hydrogen bonding polymer at a sufficient concentration to be injectable at room temperature or under operating room conditions. The multi-barrel syringe may contain a mixing chamber or inject the polymers in a manner that they mix to form the composition that will thereafter solidify. The polymers are provided in the separate barrels of the multi-barrel syringe in sufficient concentrations to form the solidifying gel composition.

Polymer gels containing only PVA exhibit lower compression modulus and an inability to mold into a self-supporting structure as a result of the common form of hydrogen-bonded interaction at comparative total polymer concentrations to the PVA/PEI gels. The PVA/PEI gels, in comparison, exhibited enhanced mechanical properties as a result of the formation of a dense network, which has been evidenced by a rapid viscosity increase upon mixing that is greater than the viscosity expected from the mixture of the two components, as well as a setting (i.e., solidifying) behavior and capability of being molded into solid gels, unlike the polymer gels containing only PVA.

The composition of the present invention may be used as a soft-tissue replacement, supplement, repair or for use in vertebroplasty. Soft tissue applications include intervertebral disc repair (e.g., nucleus pulposus replacement, corrections to the annulus fibrosus), knee meniscus repair, or as any portion of joint reconstructive systems. Uses for cosmetic and reconstructive surgery (e.g., tissue augmentation) as well as use of the composition alone, or in part, as an adhesion barrier for aiding revision surgeries are also contemplated. Other uses include as scaffolds for cells (such as, for example, mesenchymal stem cells), incorporation of growth factors (such as, for example, bone morphogenic proteins) as well as use in drug delivery.

EXAMPLES AND EXPERIMENTS

The following examples and experiments describe some of the properties of the solidifying gel compositions described herein and are only intended to assist in explaining and illustrating certain structures, features and aspects of the solidifying gel compositions and not as limiting the scope of the invention to the precise arrangements, compositions, properties or features described.

Example 1

Composition Preparation

Example 1 illustrates the formulation of one example of the composition of the present invention. PEI was combined with an aqueous solution of PVA and water as referenced in Table 1.

TABLE 1

PEI/PVA Compositions

| Component | Percentage (w/v) |
|---|---|
| PEI | 11.45 ± 2.2 |
| PVA | 22.32 ± 4.3 |
| H$_2$O | 66.23 ± 12.9 |

Compositions were prepared by mixing PEI (used as supplied; Sigma Aldrich Cat. #408727; Batch #09529 KD; M$_n$: 10 kDa) with aqueous PVA solution and water. The grade of PVA used was Mowiol 28-99 (Kuraray Specialties Europe, 99.0-99.8% degree of hydrolysis; M$_w$: 145 kDa). Before the mixture of the PEI and PVA, the two polymers were viscous but flowable or injectable. Injectable mixtures, as described herein, are capable of flowing through an aperture diameter of about 1 mm to about 5 mm at room temperature and/or under operating room conditions which are generally cooler than room temperature.

The mixture of the components was maintained at 75° C. in a water bath. The components were mixed and yielded a stiff gel or paste with an increased or higher viscosity than either of the two components alone. The separate components are injectable and the PVA and PEI solutions were intermixed using two syringes. Multi-barrel syringes equipped with mixing chamber(s) may also be used. Immediately upon mixing, the viscosity of the mixture increased noticeably, heat dissipated from the composition, and the mixture became translucent. This paste was then transferred in its green form to a sealed cylindrical mold until the time of mechanical testing. The viscosity of the mixture increased steadily until the sample solidified. Several sample compositions were produced as described above, placed in the mold and allowed to incubate for different lengths of time, anywhere from as little as 15 minutes to as much as 32 hours. The sample compositions were removed from the mold as an integral gel formed as a cylinder.

Transformation from a liquid to a solid state was not readily observed for compositions of PVA alone having a total polymer concentration of less than 32%. PVA only gel compositions of greater than 32% "sat-up" or solidified immediately following solution formation and could not flow (i.e., not injectable) under normal pressure. Whereas a 34% solution of PVA alone (Mowiol 28-99) was incapable of being stirred or injected, a 34% solution of combined PVA/PEI (22.32% PVA/11.45% PEI: 33.77% total polymer content) had an injectable green state that allows for a period of time before maturation into a stable solidified polymer network. This period of time allows the resulting composition to be injected into the human body. The composition can then solidify within the body.

Example 2

Axial Compression Testing 22.32% PVA/11.45% PEI compositions were formulated as described in Example 1 and then tested in axial compression up to 35% strain at a strain rate of 100% strain per minute. Specimen 1, 2 and 3 of Table 2 represent different samples of the sample compositions. A control composition of PVA alone at a concentration of 28% was also tested.

The different PVA/PEI sample compositions readily solidified and showed increased compressive modulus when compared to the low compressive modulus, formless PVA gels, post-molding.

TABLE 2

| | Compressive Modulus (10-20% Strain) kPa | Compressive Modulus (15-25% Strain) kPa | Compressive Modulus (20-30% Strain) kPa |
|---|---|---|---|
| Specimen 1 | 189.187 | 231.328 | 290.180 |
| Specimen 2 | 192.004 | 284.093 | 313.264 |
| Specimen 3 | 220.027 | 260.123 | 313.601 |
| Mean | 200.406 | 246.515 | 305.682 |
| Standard Deviation | 17.051 | 14.462 | 13.426 |

Table 2 shows mechanical testing data for the sample compositions that had been allowed to solidify or mature from a green state for 32 hours. FIG. 1 is a graphical representation of a representative curve of one of the specimens in Table 2.

Sample compositions were subjected to an axial compression/recovery test with a loading stage (upper portion of the curve shown in FIG. 1) and an unloading stage (lower portion of the curve shown in FIG. 1). The loading stage represents the stress versus strain when the sample composition is being compressed. The unloading stage represents the stress versus strain when the load (or pressure) is removed from the sample composition. The combined loading and unloading curve represents the "hysteresis". Generally, a gel with a more elastic response results in a small area between curves (i.e., a "tight" hysteresis"). Generally, a large area under the curve is indicative of a composition that can be elastically deformed and fails to recover following compression.

The sample compositions of Table 2 were observed to recover immediately to very close to their original height after 35% strain occurred and the load was removed (e.g., no significant height difference was observed). Recovery of samples was indicated by the tight hysteresis in FIG. 1. The loading and unloading cycles are very similar, indicating minimal plastic deformation. Following compression testing these test cylinders were visibly free from defects, cracks or fracture, indicating that no gross changes were exhibited by the samples as a result of the test.

Example 3

Formulation Comparison

The following sample compositions of increasing PEI concentration were subjected to compression testing as described in Example 2 for 4 hours and 18 hours, respectively. Each sample composition was formulated three time and then subjected to the testing procedure.

TABLE 3

| Total compositions (% w/w) | | | |
| --- | --- | --- | --- |
| Sample Type | PVA | PEI | Water |
| Control | 28.0% | 0.0% | 72.0% |
| 1x PEI | 24.8% | 11.3% | 63.8% |
| 2x PEI | 21.7% | 22.3% | 55.9% |
| 4x PEI | 15.4% | 45.0% | 39.6% |

Figure 2:
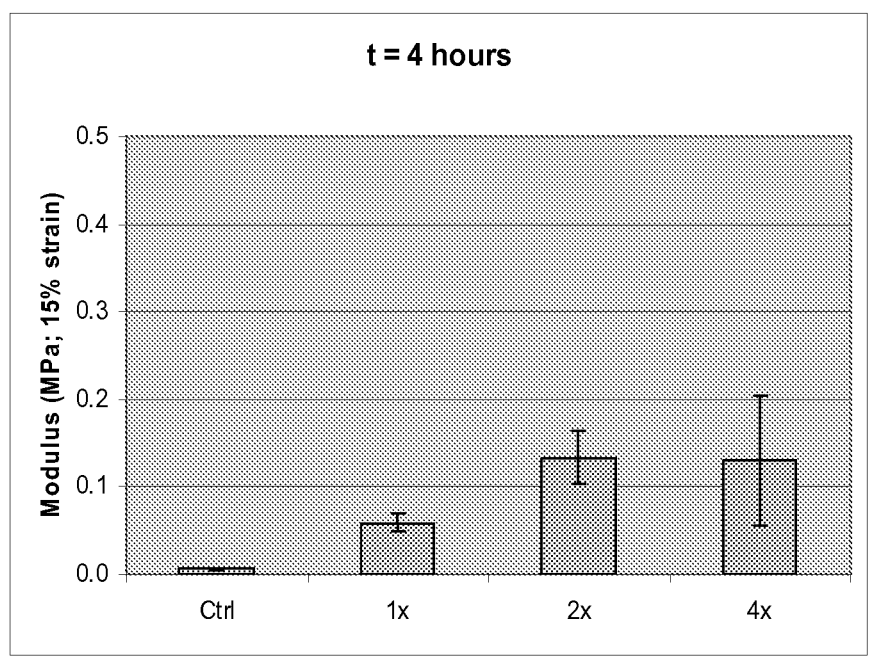
FIG. 2 is a graphical representation of the compressive modulus of sample compositions with an increasing PEI content for a 4 hour molding-time.
Figure 3:
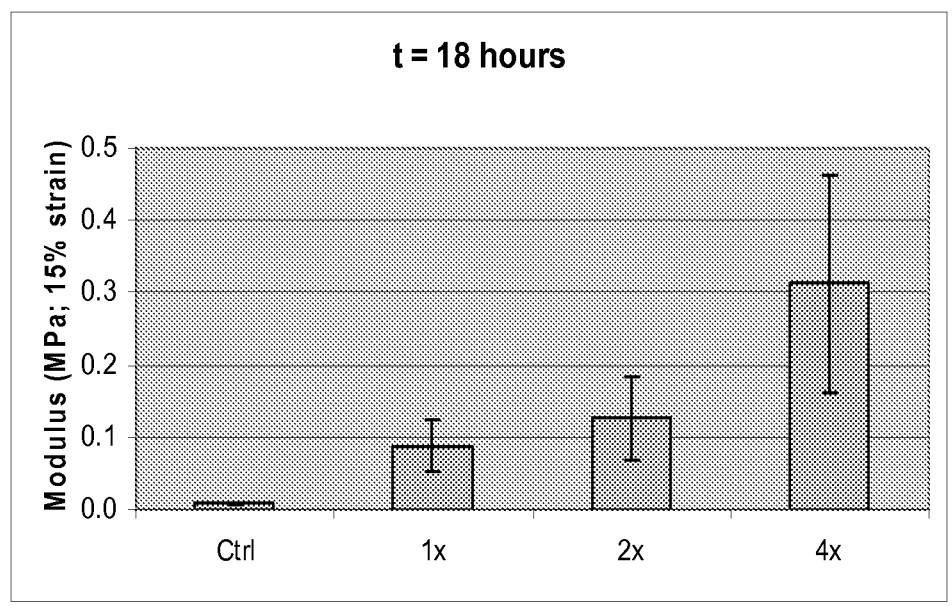
FIG. 3 is a graphical representation of the compressive modulus of sample compositions with an increasing PEI content for an 18 hour molding-time.

FIG. 2 is a graphical representation of the compression modulus for each sample composition at 4 hours. FIG. 3 is a graphical representation of the compression modulus for each sample composition at 18 hours. The straight line at the end of the each data bar in FIGS. 2 and 3 represents the variation among the sample compositions. The compressive modulus at 4 hours was significantly higher for sample compositions with a PEI component over the control composition which contained only PVA. The compressive modulus was also higher for PVA/PEI samples analyzed at 18 hours. Gels containing PEI were translucent, indicating crystallinity and were capable of being molded, while the control composition containing only PVA were transparent and did not retain the shape of the molds. Crystallinity in PVA hydrogels typically results in physical crosslinking, as hydroxyls in polymer segments bind to other hydroxyls on adjacent polymer chains. The crystallinity exhibited by blending PVA solution with PEI promotes gel formation and an increase in final compressive modulus.

Example 4

Immersion Study

Figure 4:
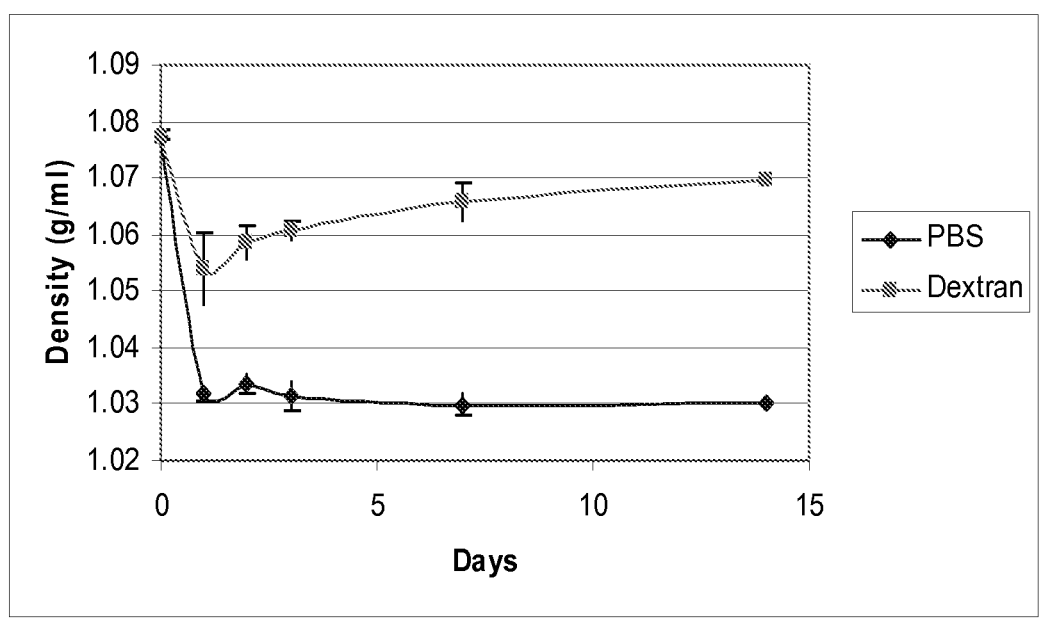
FIG. 4 is a graphical representation of the density measurement vs. immersion time for sample compositions molded for 30 minutes.

In a short-term study (e.g., 14 days; n=3), a 22.32% PVA/11.45% PEI composition was molded for 30 minutes and immersed in either phosphate buffered saline (PBS) solution, which corresponds to the typical local soft tissue environment, or an aqueous solution of Dextran (20% w/w) corresponding to the osmotic pressure of the intervertebral disc in the spine (0.1 MPa). The sample gel compositions were shown to increase in mass and decrease in density with the uptake of water. FIG. 4 shows the density of the sample composition over time. Following an initial drop in density, the Dextran-immersed composition was able to recover to within 0.01 g/ml of the starting density. However, the PBS-immersed composition was unable to recover its density following its initial drop in density.

Figure 5:
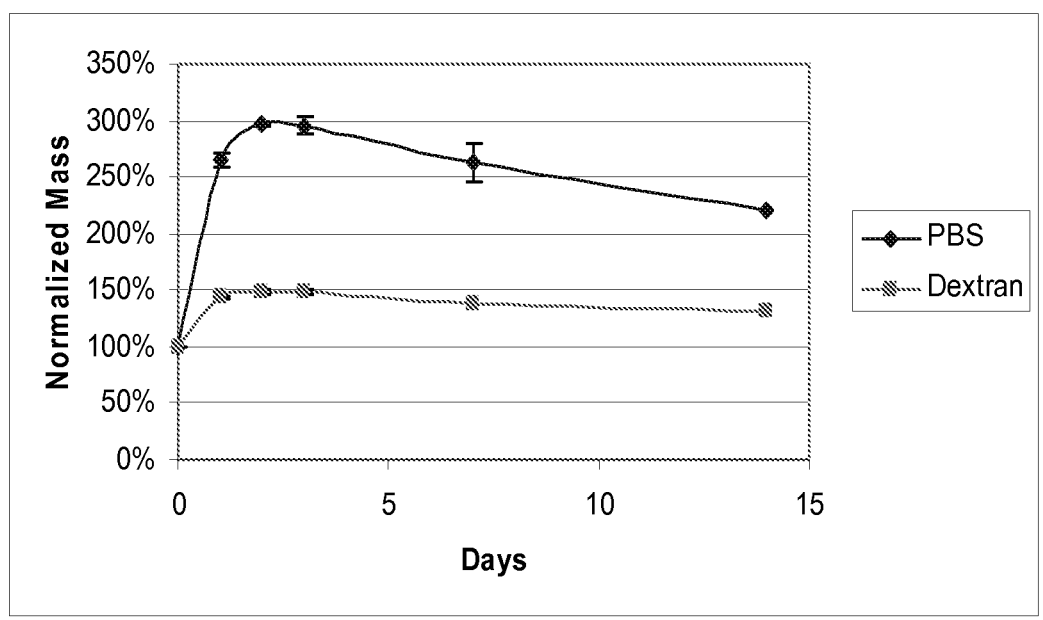
FIG. 5 is a graphical representation of the normalized mass vs. immersion time for sample compositions molded for 30 minutes.

FIG. 5 shows the normalized mass of the compositions over time. The Dextran-immersed composition demonstrated a normalized mass that remained stable over time, whereas the PBS-immersed composition lost mass over time. The data in both FIGS. 4 and 5 demonstrate that the composition that was immersed in Dextran was more stable than the composition immersed in PBS.

Example 5

Alternate Formulations

Compositions of PEI and polyethylene oxide (PEO) were produced using PEO (Fluka#: 81280; $M_n$=10 kDa) mixed with PEI. PEI was mixed with 33% PEO solution in a 1:1 ratio by mass. The mixture resulted in the formation of a translucent solution of higher viscosity than either of the PEI or PEO components alone. The resulting composition solidified upon mixing of the PEI with the PEO.

Example 6

Calorimetry

Differential Scanning Calorimetry (DSC) was performed in order to compare crystallization temperatures for samples of PVA/PEI gel compositions ("Test Samples") to gel compositions formed of only PVA (i.e., no PEI) ("Control Samples"). As demonstrated by this study, crystallization temperatures were shown to increase with the addition of PEI.

TABLE 4

| Compositions* | |
| --- | --- |
| Test Samples | Control Samples |
| 20% PVA | 25% PVA |
| 20% PEI | 0% PEI |
| 60% H$_2$O | 75% H$_2$O |

*Composition percentages are on a w/w basis and were selected in order to keep the PVA to water ratio constant.

Figure 6:
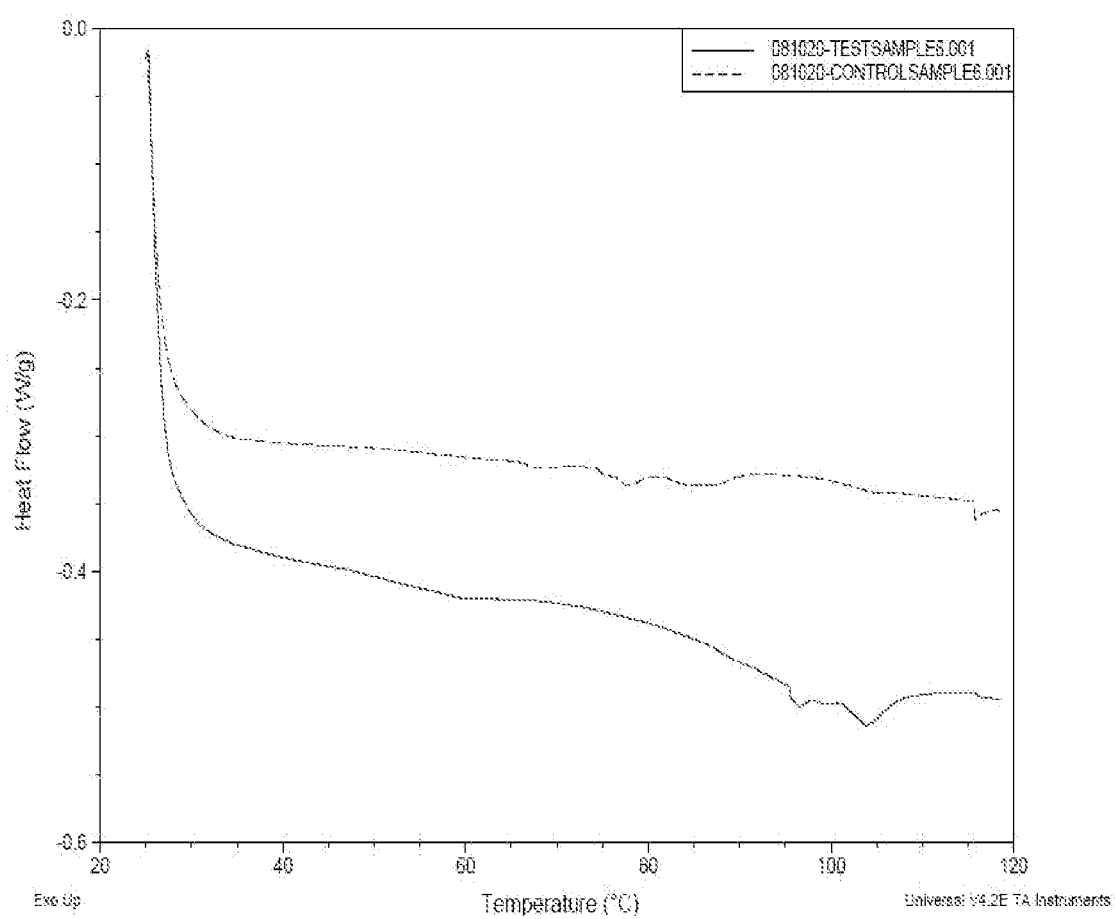
FIG. 6 is a graphical representation of a representative DSC scan for Test Samples and Control Samples.

DSC for Test Samples exhibited an endotherm at just over 90° C., while Control Samples exhibited endotherms in the 75°-85° C. range. See FIG. 6. A higher crystallization temperature coupled with a larger endotherm is an indicator of a more stable gel. The addition of PEI to PVA is therefore desirable in that it forms a crystalline network that is less likely to "melt out." When a gel composition "melts" the bonds in the crystalline network are broken. The PVA/PEI Test Sample is a stable gel composition of high compressive modulus and a higher endotherm.

The embodiments set forth above, among those made apparent from the preceding description, are efficiently attained and, since certain changes may be made in carrying out the above method of forming and in the resulting composition without departing from the spirit and scope of the invention, it is intended that all matter contained in the above description shall be interpreted as illustrative and not in a limiting sense.

It will also be understood that the embodiments presented herein are intended to cover all of the generic and specific features of the invention herein described and all statements of the scope of the invention which, as a matter of language, might be said to fall therebetween. Particularly it is to be understood that in said embodiments, ingredients or compounds recited in the singular are intended to include compatible mixtures of such ingredients.

It will be appreciated by those skilled in the art that changes could be made to the embodiments described above without departing from the broad inventive concept thereof. It is understood, therefore, that this invention is not limited to the particular embodiments disclosed, but is intended to cover modifications within the spirit and scope of the present invention as defined by the appended claims.

The invention claimed is:

1. A polymer gel composition comprising
   polyethylene imine, the polyethylene imine being injectable prior to mixing, and
   an aqueous polyvinyl alcohol solution comprising polyvinyl alcohol, the aqueous polyvinyl alcohol solution being injectable prior to mixing,
   wherein the composition has a greater viscosity than either of the polyethylene imine or the aqueous polyvinyl alcohol solution alone,
   wherein the polymer gel composition is a hydrogen-bonded physically crosslinked polymer gel, and is injectable immediately after mixing of the polyethylene imine and the aqueous polyvinyl alcohol solution,
   wherein the polyethylene imine is from about 9.25% (w/w) to about 13.65% (w/w) and the polyvinyl alcohol is from about 18.02% (w/w) to about 26.62% (w/w),
   wherein a solution of a single phase is formed when the polyethylene imine is mixed with the polyvinyl alcohol.

2. The composition of claim 1, wherein the aqueous polyvinyl alcohol solution is blended with polyvinyl pyrrolidone.

3. The composition of claim 1, wherein the polyethylene imine is from about 10.2% (w/w) to about 12.4% (w/w).

4. The composition of claim 1, wherein the polyethylene imine is from about 11.4% (w/w) to about 11.8% (w/w).

5. The composition of claim 1, wherein the polyvinyl alcohol is from about 19.7% (w/w) to about 23.3% (w/w).

6. The composition of claim 1, wherein the polyvinyl alcohol is from about 22.1% (w/w) to about 22.6% (w/w).

7. A polymer gel composition comprising about 9.25% (w/w) to about 13.65% (w/w) polyethylene imine and about 18.02% (w/w) to about 26.62% (w/w) polyvinyl alcohol, wherein the polymer gel composition is a hydrogen-bonded physically crosslinked polymer gel, wherein the composition has a greater viscosity than either of the polyethylene imine or the polyvinyl alcohol component alone and is injectable immediately after mixing of the polyethylene imine and the polyvinyl alcohol, and wherein a solution of a single phase is formed when the polyethylene imine is mixed with the polyvinyl alcohol.

8. A kit for forming a polymer gel composition comprising:
   at least one first container loaded with polyethylene imine at a sufficient concentration to be injectable at room temperature or under operating room conditions, and
   at least one second container loaded with polyvinyl alcohol at a sufficient concentration to be injectable at room temperature or under operating room conditions,
   wherein the polyethylene imine and the polyvinyl alcohol are supplied in the first and second containers in sufficient concentrations and amounts so that upon mixing the polyethylene imine and the polyvinyl alcohol the resulting polymer gel composition is a hydrogen-bonded physically crosslinked polymer gel and is injectable for a predetermined amount of time and thereafter solidifies into a moldable form,
   wherein the polyethylene imine is from about 9.25% (w/w) to about 13.65% (w/w), and the polyvinyl alcohol is from about 18.02% (w/w) to about 26.62% (w/w),
   wherein a solution of a single phase is formed when the polyethylene imine is mixed with the polyvinyl alcohol.

9. The kit of claim 8, wherein the kit further comprises a multi-barrel syringe wherein the first container is one of the barrels of the multi-barrel syringe and the second container is one of the other barrels of the multi-barrel syringe.

10. The kit of claim 8, wherein the polyvinyl alcohol is blended with polyvinyl pyrrolidone.

11. The kit of claim 8, wherein the polyethylene imine is from about 10.2% (w/w) to about 12.4% (w/w).

12. The kit of claim 8, wherein the polyethylene imine is from about 11.4% (w/w) to about 11.8% (w/w).

13. The kit of claim 8, wherein the polyvinyl alcohol is from about 19.7% (w/w) to about 23.3% (w/w).

14. The kit of claim 8, wherein the polyvinyl alcohol is from about 22.1% (w/w) to about 22.6% (w/w).

15. The kit of claim 8, wherein the predetermined amount of time is up to about four hours.

16. The kit of claim 8, wherein the predetermined amount of time is less than thirty minutes.

* * * * *